United States Patent [19]
Pidoux et al.

[11] Patent Number: 5,537,811
[45] Date of Patent: Jul. 23, 1996

[54] METHOD FOR CATEGORIZING YARN DEFECTS AND CLEANSING YARN

[75] Inventors: Roger Pidoux, Zurich; Peter Haldemann, Wollerau, both of Switzerland

[73] Assignee: Roospark Ag, Wollerau, Switzerland

[21] Appl. No.: 281,862

[22] Filed: Jul. 28, 1994

Related U.S. Application Data

[63] Continuation of Ser. No. 942,268, Sep. 9, 1992, abandoned.

[30] Foreign Application Priority Data

Sep. 11, 1991 [CH] Switzerland ............................ 2-673/91

[51] Int. Cl.[6] ................................. D01H 7/46; D01H 7/92
[52] U.S. Cl. ................................. 57/264; 28/226; 57/265; 73/160
[58] Field of Search ......................... 57/264, 265; 28/226; 73/160

[56] References Cited

U.S. PATENT DOCUMENTS

| | | | |
|---|---|---|---|
| 4,045,659 | 8/1977 | Akagawa et al. | 73/160 X |
| 4,430,720 | 2/1984 | Aemmer | 73/160 X |
| 4,491,831 | 1/1985 | Sakai et al. | 57/265 X |
| 4,764,876 | 8/1988 | Whitener et al. | 73/160 X |
| 4,817,425 | 4/1989 | Ueda | 57/264 X |
| 5,119,308 | 6/1992 | Samoto | 57/265 X |
| 5,181,374 | 1/1993 | Aeppli | 57/264 |

FOREIGN PATENT DOCUMENTS

| | | |
|---|---|---|
| 0005083 | 10/1979 | European Pat. Off. . |
| 0415222 | 3/1991 | European Pat. Off. . |
| 0439767 | 8/1991 | European Pat. Off. . |
| 1900312 | 8/1969 | Germany . |
| 3438962 | 4/1986 | Germany . |
| 3928417 | 3/1990 | Germany . |
| 4003810 | 6/1990 | Germany . |
| 477573 | 8/1969 | Switzerland . |

*Primary Examiner*—William Stryjewski
*Attorney, Agent, or Firm*—Walter C. Farley

[57] ABSTRACT

A method and apparatus for simultaneously cleansing and grading yarn produced by a spinning or spooling machine with a plurality of spindles or primary spools. One spindle processor is associated with each spindle. The spindle-processor grades in a grading plane containing a cleansing envelope. All yarn defects located outside the cleansing envelope in the grading plane are considered unacceptable defects and are excised from the yarn.

14 Claims, 3 Drawing Sheets

METHOD FOR CATEGORIZING YARN DEFECTS AND CLEANSING YARN

This is a continuation of Ser. No. 07/942,268 filed on Sep. 9, 1992, now abandoned.

FIELD OF THE INVENTION

The invention relates to a method and apparatus for classifying or grading and cleaning yarns.

BACKGROUND OF THE INVENTION

Threads or yarns produced from spindles in ring or rotor spinning frames are "cleaned" i.e., controlled for thickness, before being wound on spools. Thick and thin parts outside tolerances—i.e. unacceptably defective—are excised and the sections on either side of the removed flaw are rejoined by knotting or splicing. Those flaws which deviate greatly from the nominal value, i.e., from the rated yarn thickness, are excised even when they are comparatively short, whereas defects deviating comparatively slightly from the nominal value are excised only if they are comparatively long. Accordingly, cleansing is accomplished when a yarn defect exceeds compound values formed on one hand by deviation from the nominal yarn thickness and on the other hand by the length of the deviation.

Moreover, such yarn defects can be "graded". This means that a two-dimensional reference is associated with each thick or thin length—that is, with each acceptable and unacceptable defect—which reflects both the deviation from the nominal value and how long the deviation is. As a result, a curve can be developed such that, in a two-dimensional plane formed from the two-dimensional reference called the "grading plane", there will be an arbitrary curve determining the elimination from the yarn of all thick and thin lengths outside the cleansing "envelopes" and hence which are considered unacceptable defects.

Depending on how the two-dimensional numerical reference and the shape of the cleansing curve are constituted (the two magnitudes can be selected in different ways), it is possible to manufacture yarn with the same thickness distribution and with significantly more or fewer knots or splices. Accordingly, the fewer knots or splicings which have been selected per unit length of yarn, and the closer together the cleansing boundaries of the unacceptable defects, the higher the yarn quality.

Swiss patent 477,573 describes apparatus for a yarn cleanser wherein the yarn thickness is converted into an electrical signal which then is fed to a damping circuit with an adjustable time-constant and then to a Schmitt trigger of which the response threshold also is adjustable. Signals thus processed which exceed a specified pulse height, representing the magnitude of the yarn defect, actuate a cutting and knot-tieing mechanism. Accordingly, only those yarn defects are detected which are considered unacceptable by the apparatus. Depending on the time-constant, short thick segments and long slowly growing thick segments are, respectively, substantially undamped and substantially damped before being fed to the Schmitt trigger, as a result of which short segments are excised only if there is substantial deviation from the nominal value, while long, gradually growing segments on the other hand are excised even if they deviate only slightly from the nominal value as compared with short thick segments. As stated above, this is precisely the behavior which is desired. However, this apparatus cannot detect excessively thin segments.

Adjusting this apparatus by changing the setpoints of damping and response threshold of the Schmitt trigger for a new sort of yarn is fairly time-consuming. Moreover, this apparatus is unable to grade because it can ascertain only values that make the Schmitt trigger respond, but cannot recognize acceptable yarn defects. Thus, perspective is lacking on the distribution of the accepted yarn defects and the cut yarn defects, and no conclusion may be drawn as to how close this apparatus has come to the optimum cleansing boundary.

"Selectors" are also known. These are cards receiving the actually occurring yarn defects in two dimensions, arranged by thickness deviation and yarn defect length. They are used to determine the unacceptable defects for yarn cleansing. Thus, a yarn cleansing apparatus must operate in such a way that it shall excise from the yarn all defects ascertained by the selector as being unacceptable.

European patent document B 0 153 350 discloses a grading method and the associated apparatus operating with first processors to periodically monitor an ever larger number of spindles, illustratively stated as 24, and a central processor. The grading of spindle-produced yarn always is carried out within a limited monitoring time interval, whereupon the yarn of the next spindle is graded, and so forth, until, after a comparatively long time has elapsed, the yarn from the original spindle is graded again. Hence, grading is carried out only by "sampling" over a small portion of the spindle operating time so that the checking does not detect all defects but rather is fairly statistical in nature and is useful only in steady-state operation of the individual spindles. To reduce the unreliability of such sampling, especially when starting up a spindle, the periodic checking of all other spindles is suspended during the start-up time of a spindle until it has reached its steady state. This procedure is easily carried out with a spinning machine because the spindles are started up consecutively and no more than one is starting at any given time. On the other hand, such a procedure entails further lapses in grading time for the other spindles. Because such apparatus checks the spindle-made yarn for its thickness only briefly, it is unsuitable to grade yarn for which all unacceptable defects must be detected.

SUMMARY OF THE INVENTION

Accordingly, it is an object of the invention to provide a method and apparatus for a spinning machine operating with a plurality of spindles to simultaneously grade all yarn defects and to cleanse the yarn from each spindle from all unacceptable defects.

Briefly described, the invention comprises a method for grading and cleansing yarns at a spinning or spooling machine with a plurality of spindles or spools each producing yarn having yarn defects of various lengths and thicknesses. The method comprises continuously detecting and supplying to a spindle processor having a memory test values of yarn thickness and yarn defect length for each spindle and determining for each yarn defect a two-dimensional grading definition or evaluation based on yarn-thickness deviation from the nominal yarn thickness and the length of each yarn defect. A count is accumulated in a plurality of cells in the memory of the number of yarn defects categorized in each of a plurality of defect grading definitions, each defect definition corresponding to a region in a two-dimensional grading plane having a threshold line defining a cleansing envelope. All unacceptable yarn defects located in the grading plane outside the cleansing envelope are excised from the yarn.

BRIEF DESCRIPTION OF THE DRAWINGS

The invention is elucidated below with reference to the accompanying drawings, wherein.

DESCRIPTION OF THE PREFERRED EMBODIMENTS

Identical components are denoted in all Figures by the same references numerals.

Figure 1:
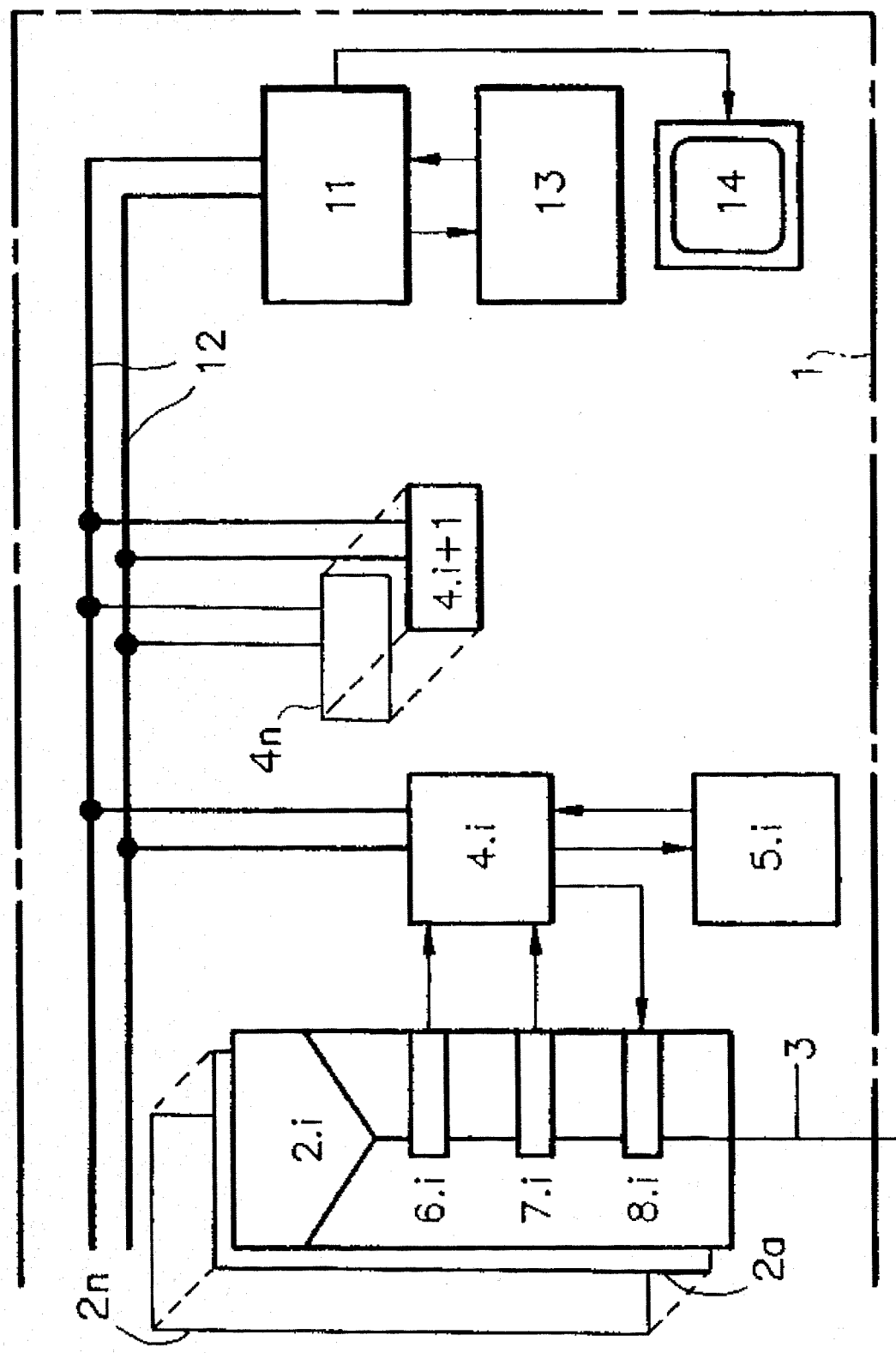
FIG. 1 is a schematic circuit diagram of an apparatus in accordance with the invention.

An apparatus in accordance with the invention is shown by a functional block diagram in FIG. 1. It consists of a spinning or spooling machine 1, only spinning machines being discussed herein. As regards spooling machines, the spindles each time are replaced by (primary) spools. Each spool 2 producing the yarn 3 is equipped with its own spindle processor 4 having a spindle memory 5. The spindle processor 4 continuously receives test values regarding the thickness of yarn 3 from a yarn-thickness tester 6 and test values of yarn length from a yarn-length tester 7. Spindle processor 4 ascertains which yarn defects are acceptable and causes a cutter 8 to excise the unacceptable yarn defects from the yarn 3 and further causes the yarn 3 to be re-knotted or re-spliced. In principle, several spindles 2, 2a, . . . 2n alternatively may be connected to and monitored by a single spindle processor 4 which, in that event, must have much higher computing capacity to ensure constant monitoring of these spindles.

In FIG. 1, the spindle processor belonging to the next successive spindle 2a following spindle 2 is identified as 4a.

In addition, a central processor 11 is present at the spinning machine and is connected to all spindle processors 4, 4a, . . . 4n through a bus 12, processor 11 having an associated central memory 13 and a display 14, such as an image screen, and carrying out overriding control procedures and display outputs.

Figure 2:
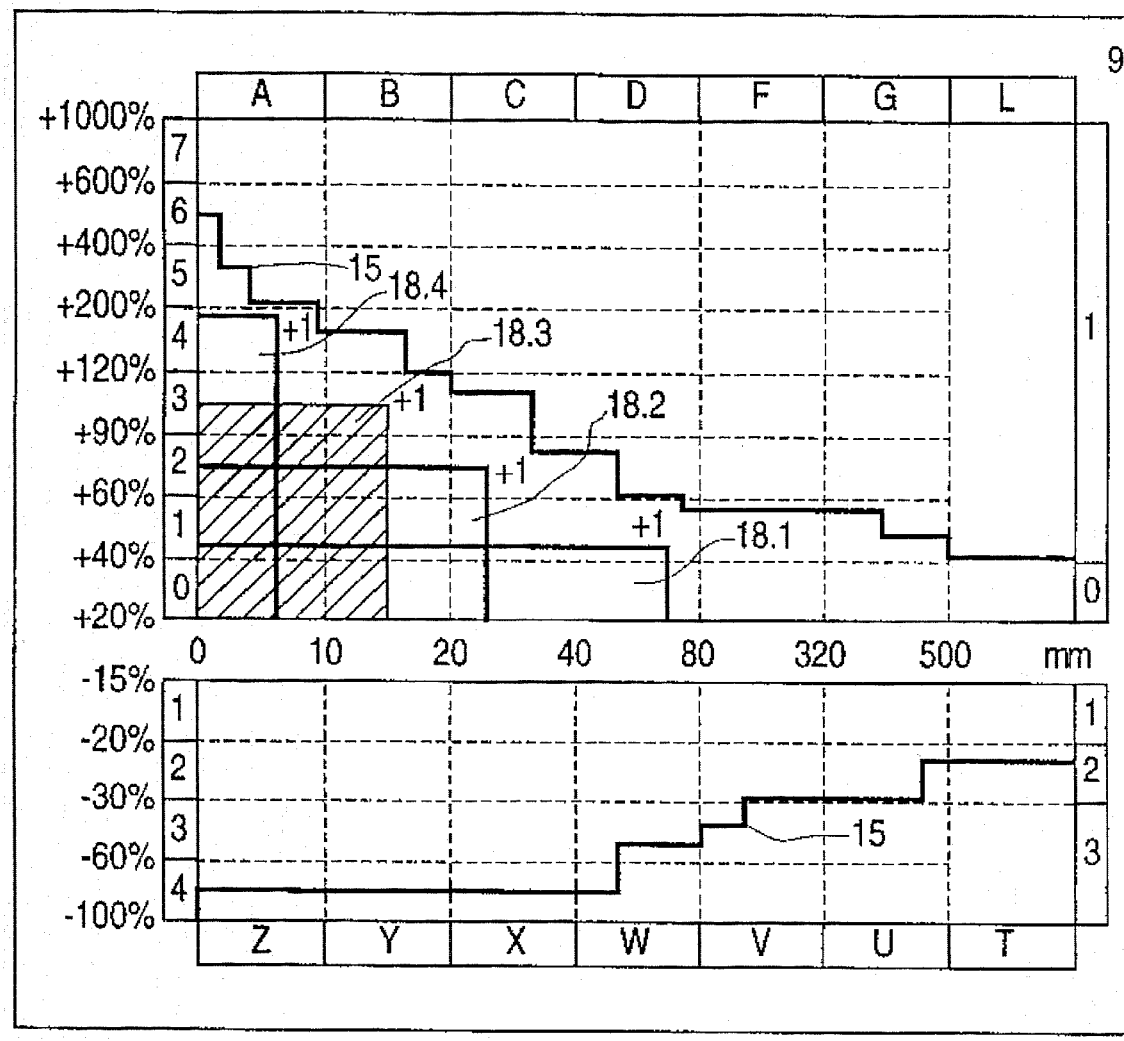
FIG. 2 is an illustration of a typical grading diagram in accordance with the invention.

FIG. 2 explains the analysis of the data gathered by a spindle processor 4. A "grading plane" 9 shown therein is formed. The spindle processor 4 determines two-dimensional grading features for each yarn defect as a function of the deviation of yarn thickness from the nominal value and the length of the yarn defect. In the example shown, the numbers 0 through 7 are used for different degrees of thickness deviation and the lengths of these deviations are identified by letters A through L (for positive thickness deviations) and T through Z (for negative thickness deviations). The thickness deviations are stated in percent (%), the yarn defect lengths in mm. For each two-dimensional grading symbol (for instance A3, which in this example means a defect length between 0 and 10 mm and a thickness deviation between +90% and +120%) there is in the grading plane 9 a cell 10. The spindle processor each time notices in these cells 10 the number of yarn defects for which the grading symbol belonging to a specific cell 10 was found. The processor therefore increases the number of the previously accrued yarn defects in a memory cell or portion which corresponds to the cell 10 designated by the particular grading symbol whenever a yarn defect with this grading symbol is found. The yarn defect is graded thereby.

A heavy solid line is shown in the grading plane 9 and separates the acceptable yarn defects from the unacceptable ones. This is the "cleansing envelope" 15. As a rule, this line consists of a stepped sequence of connected half-rectangles. The unacceptable yarn defects are located outside the cleansing envelope 15 (i.e., above it and to the right) and must be excised from the yarn.

Spindle processor 4 can also relate the number of yarn defects in each cell 10 to a predetermined length of the finished yarn 3. Illustratively, the number may always refer to 10 km of yarn 3.

The grading plane 9 with the numbers of yarn defects for a predetermined length of the yarn 3 can be displayed for each spindle by central processor 11 on screen 14.

Figure 3:
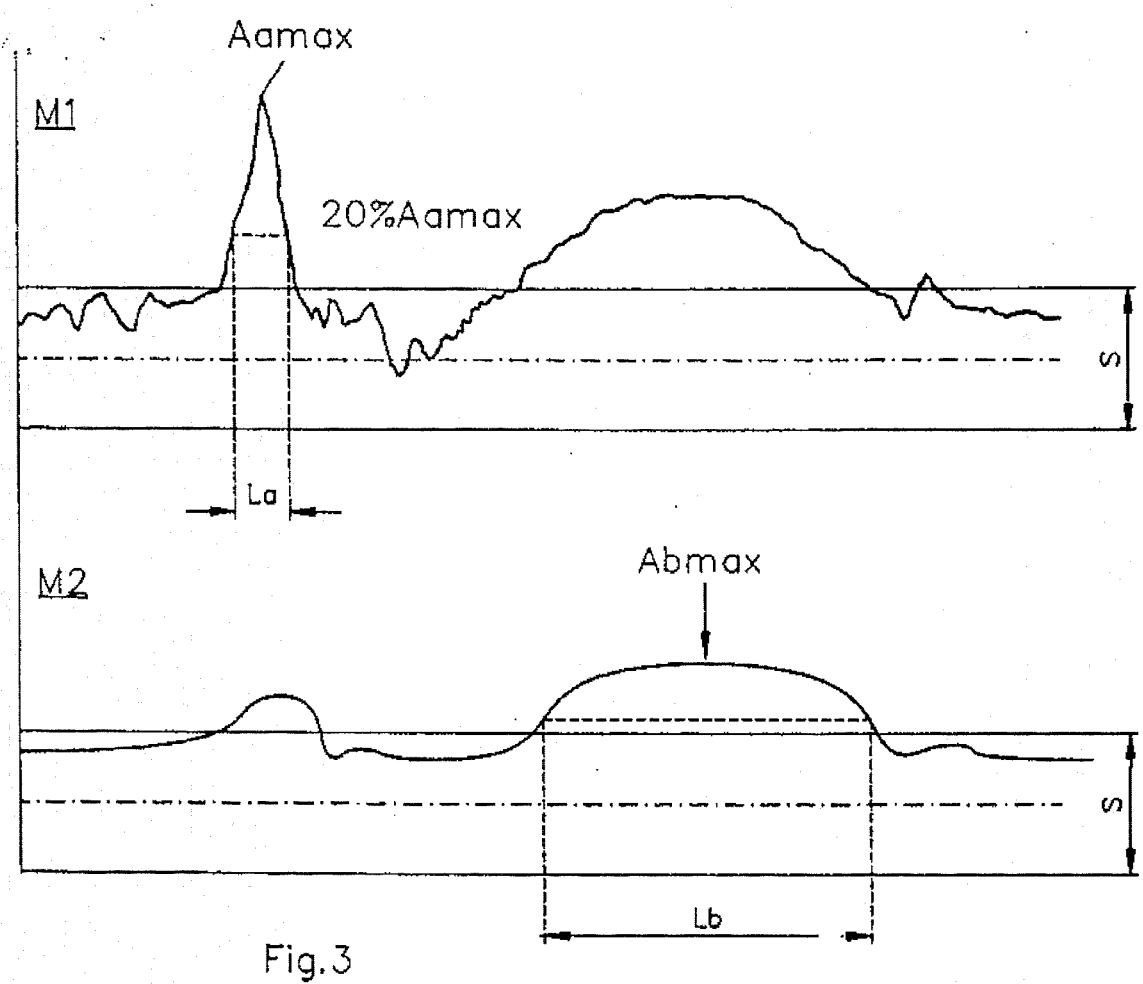
FIG. 3 shows damped and undamped recording of yarn defects.

The following symbols are used only in relation to FIG. 3: nominal thickness S, maximum deviation Amax from the nominal thickness S and yarn defect length L. The undamped and clearly damped test values are respectively identified as M1 and M2. The subscript "a" in such symbols denotes yarn defects with a steep edge and the subscript "b" denotes yarn defects with a shallow or gradual edge.

The thickness test values for a steep edge can be fed as undamped test values M1 to spindle processor 4 and, for yarn defects with a shallow edge, as damped test values M2. As a result, the undamped test value M1 must be large for short yarn defects in order to exceed the cleansing envelope 15 (FIG. 2). On the other hand, shallow edge defects must be present over a considerable length in order for their damped test value M2 to exceed the cleansing envelope 15. This is the desired behavior.

As shown by FIG. 3, spindle processor 4 makes use of the length L as the yarn defect length, where said length L is such that the yarn-thickness deviation from the nominal value exceeds a predetermined fraction of the maximum deviation Amax of the yarn-thickness from the nominal value S for the particular yarn defect. For example, that length L is used as the particular defective yarn-length at which the yarn-thickness deviation exceeds ⅕ of the maximum yarn-thickness deviation Amax from the nominal value at the particular yarn defect. However, other magnitudes also may be used.

Figure 4:
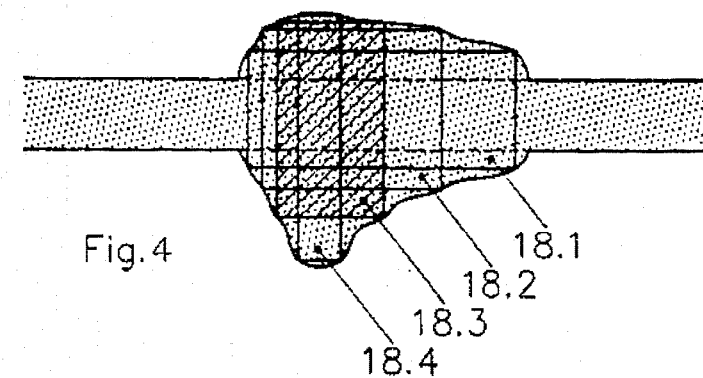
FIG. 4 is a diagram showing how a yarn defect is resolved into constituent defects.

As illustratively shown by FIG. 4, a yarn defect can be divided into defect segments 18.1–18.4 which can be represented as the shown annular regions having axes parallel to the yarn axis, shown in the yarn defect cross-section taken in a plane parallel to the yarn axis. For each defect segment 18.1–18.4, a grade definition can then be computed based on the length of each annular region and the deviation of the annulus radius from the nominal yarn thickness value. This is carried out with the defect segments 18.1 through 18.4 of FIG. 4, which are plotted as in FIG. 2. Thereupon the number of defects is raised by unity in the corresponding memory cell 10. A yarn defect is deemed unacceptable and its excision must be carried out by the spindle processor 4 when at least one of its defect segments 18.1–18.4 evinces a grade definition outside the cleansing envelope 15. This is not the case for the defect segments 18.1–18.4 in the grading plane 9 with the specific cleansing envelope 15 shown therein. The recording of defective segments 18 described herein offers more detailed grading.

When a grading plane 9 has been made statistically significant by the entry of large enough numbers of yarn defects into the memory portions corresponding to cells 10, the cleansing envelope 15 may be improved by being moved outward in the vicinity of cells 10 displaying large numbers of yarn defects and inward in the vicinity of cells 10 with low numbers of yarn defects. In this manner the number of required knots or splices is reduced, and for the same quantity of initial material, the length of the yarn to be made is increased.

In this manner the method and apparatus of the invention make it possible to also simultaneously cleanse and grade all yarns 3 simultaneously produced at a spinning machine 1 of many spindles 2. Thereby the object of the invention is achieved.

The yarn defects are entered in a grading plane 9 containing a cleansing envelope 15 by means of which the unacceptable defects are determined. Following a given start-up time of the spindles 2, the apparatus allows so changing the cleansing envelope 15 that the number of knots or splices in the yarn 3 is minimized while observing the manufacturing conditions for the yarn 3, as a result of which the quality and the finished length of yarn is improved with the same amount of initial material being used.

We claim:

1. A method for grading and cleansing yarns (3) at a spinning or spooling machine (1) with a plurality of spindles (2) or spools each producing yarn having yarn defects of various lengths and thicknesses, the method comprising the steps of continuously detecting and supplying to a spindle processor (4) having a memory (5) test values of yarn thickness, yarn defect thickness and yarn defect length (3) for each spindle or spool (2), first determining for every yarn defect a grading definition based on both the length and thickness of each defect wherein deviation (A) of the defect from a nominal yarn thickness (S) exceeds a predetermined fraction of a maximum yarn thickness deviation from the nominal value at that specific yarn defect, assigning in the processor each said defect to one of a plurality of categories defined by ranges of values of yarn defect length and yarn defect thickness, accumulating in a plurality of cells in the memory a count of the number of yarn defects categorized in each defect category, establishing a threshold in the memory to distinguish between acceptable and unacceptable yarn defect categories, after accumulating a count of defects, excising from the yarn (3) those yarn defects assigned to unacceptable yarn defect categories.

2. A method according to claim, 1 and including correlating in the spindle processor (4) the number of yarn defects in each cell (10) with a predetermined length of the yarn (3) being produced.

3. A method according to claim 1 in a system including a central processor (11) connected to receive defect count and category information from spindle processors, the central processor having a display with an image screen, the method comprising displaying on the image screen a representation of the defect categories together with the number of yarn defects of yarn produced by each spindle or spool (2) in each category.

4. A method according to claim 1 and including continuously producing and delivering to the spindle processor undamped test values (M1) and damped test values (M2) of the yarn-thickness deviation (A) from the nominal value (S).

5. A method according to claim 4 wherein the undamped test values (M1) delivered to the spindle processor (4) represent yarn defects having steep edge characteristics.

6. A method according to claim 4 wherein the damped test-values (M2) delivered to the spindle processor (4) represent yarn defects having gradually changing characteristics.

7. A method according to claim 1 wherein the predetermined fraction is ⅕.

8. A method according to claim 1 wherein the step of accumulating includes increasing the number of defects by unity in each cell (10) representing a category to which a defect is assigned.

9. A method according to claim 1 wherein the step of accumulating includes increasing the number of defects by unity in each cell (10) representing a category to which a defect is assigned.

10. A method according to claim 9 wherein a yarn defect is considered unacceptable and the spindle-processor (4) causes its excision when at least one of its defect segments (18) evinces a grade definition outside the cleansing envelope (15).

11. A method according to claim 1 wherein a spindle-processor (4) serves a plurality of spindles or spools (2).

12. A method for grading and cleansing yarns (3) at a spinning or spooling machine (1) with a plurality of spindles (2) or spools each producing yarn having yarn defects of various lengths and thicknesses, the method comprising the steps of continuously detecting and supplying to a spindle processor (4) having a memory (5) test values of yarn thickness, yarn defect thickness and yarn defect length (3) for each spindle or spool (2), first analyzing every yarn defect to determine for each defect a grading definition based on yarn defect thickness deviation (A) from nominal yarn thickness (S) and the length (L) of each yarn defect, the analysis including dividing a yarn defect into defect segments (18), assigning in the processor each said defect to one of a plurality of categories defined by ranges of values of yarn defect length and yarn defect thickness, accumulating in a plurality of cells in the memory a count of the number of yarn defects categorized in each defect category, establishing a threshold in the memory to distinguish between acceptable and unacceptable yarn defect categories, after accumulating a count of defects, excising from the yarn (3) all yarn defects assigned to unacceptable yarn defect categories.

13. A method according to claim 11 wherein, in the step of assigning, the categories of defect segments (18) are defined by annular regions having axes parallel to a longitudinal yarn axis.

14. A method for grading and cleansing yarns (3) at a spinning or spooling machine (1) with a plurality of spindles (2) or spools each producing yarn having yarn defects of various lengths and thicknesses, the method comprising the steps of continuously detecting and supplying to a spindle processor (4) having a memory (5) test values of yarn thickness, yarn defect thickness and yarn defect length (3) for each spindle or spool (2), determining for every yarn defect a grading definition based on both a yarn defect thickness deviation (A) from a nominal yarn thickness (S) and a length (L) of each yarn defect, assigning in the processor each said defect to one of a plurality of categories defined by ranges of values of yarn defect length and yarn defect thickness, accumulating in a plurality of cells in the memory a count of the number of yarn defects categorized in each defect category, establishing a threshold in the memory to distinguish between acceptable and unacceptable yarn defect categories, after accumulating a count of defects, excising from the yarn (3) all yarn defects assigned to unacceptable yarn defect categories, and after the analysis has been made statistically significant by the entry of enough large numbers of yarn defects into the cells (10), adjusting the threshold to include as unacceptable yarn defect categories more cells with large numbers of yarn defects and fewer cells with low numbers of yarn defects.

* * * * *

UNITED STATES PATENT AND TRADEMARK OFFICE
CERTIFICATE OF CORRECTION

PATENT NO. : 5,537,811
DATED      : July 23, 1996
INVENTOR(S): Roger Pidoux & Peter Haldemann It is certified that error appears in the above-indentified patent and that said Letters Patent is hereby corrected as shown below:

On the title page, item [73] should read:
[73]   Assignee:  Zellweger Luwa AG, Uster, Switzerland Signed and Sealed this Eighteenth Day of February, 1997

*Attest:*

BRUCE LEHMAN

*Attesting Officer*     *Commissioner of Patents and Trademarks*